United States Patent [19]
Holden

[11] Patent Number: 5,779,655
[45] Date of Patent: Jul. 14, 1998

[54] FLEXIBLE AND REMOVABLE LEG CAST/ BRACE HANDLE

[76] Inventor: Jeffrey H. Holden, 1040 Arbor Rd., No. A, Winston-Salem, N.C. 27104

[21] Appl. No.: 743,032

[22] Filed: Nov. 4, 1996

Related U.S. Application Data

[60] Provisional application No. 60/006,299 Nov. 6, 1995.

[51] Int. Cl.⁶ .................. A61F 5/00; A61F 5/04
[52] U.S. Cl. .................. 602/5; 602/23; 602/62; 128/582
[58] Field of Search .................. 602/3–6, 23, 27, 602/60–62; 128/882, DIG. 15; 294/147, 157, 149; 606/201, 203; 224/150, 917, 250, 578–582, 602, 128, 224

[56] References Cited

U.S. PATENT DOCUMENTS

| | | |
|---|---|---|
| 4,014,327 | 3/1977 | Spiro . |
| 4,019,503 | 4/1977 | Smith . |
| 4,470,528 | 9/1984 | Dyess . |
| 4,751,923 | 6/1988 | Marino .................. 602/4 |
| 4,854,313 | 8/1989 | Kloepper . |
| 4,863,083 | 9/1989 | Chen .................. 224/250 X |
| 5,592,953 | 1/1997 | Delao .................. 128/882 |
| 5,611,427 | 3/1997 | Bigham .................. 224/917 X |

*Primary Examiner*—Richard J. Apley
*Assistant Examiner*—Denise Pothier
*Attorney, Agent, or Firm*—Wigman, Cohen, Leitner & Myers, P.C.

[57] ABSTRACT

A flexible and removable leg cast/brace handle comprises a first strap and a second strap permanently interconnected by a longitudinally extending third strap, and at least one loop handle being connected to the third strap. In one embodiment, a single loop handle extends between the first strap and the second strap. In another embodiment, a single handle is connected to the first strap, the second strap, or the third strap, or to a combination thereof. In still another embodiment, two loop handles are provided, each handle extending between an intermediate portion of the third strap and a respective one of the first and second straps.

17 Claims, 2 Drawing Sheets

FLEXIBLE AND REMOVABLE LEG CAST/BRACE HANDLE

CROSS-REFERENCE TO RELATED APPLICATION

This application is based on U.S. provisional patent application Ser. No. 60/006,299 filed Nov. 6, 1995, and entitled "The Flexible and Removable Leg Cast/Brace Handle."

TECHNICAL FIELD

The present invention generally relates to a flexible and removable leg cast/brace handle which can be used by a person who has injured a leg to manipulate or otherwise move or lift the injured leg using only one hand, thereby freeing the other hand for balancing or other use.

BACKGROUND OF THE INVENTION

Typically, when a person injures a leg, the use of a brace or cast for a substantial period of time is necessary while the person recuperates from the injury. In such cases, the person's muscles, and in particular, the leg muscles, are either too weak to lift the leg, including the cast or brace, due to the trauma from the injury, or due to the weight of the cast or brace. As a result, such persons require assistance when it is necessary to manipulate or otherwise move or lift the leg. The requirement to manipulate or otherwise move the leg arises frequently in the course of a day, such as when the person desires to arise from a bed or couch, recline on a bed or couch, or move from place to place. In the prior art, attempts have been made to facilitate movement and manipulation of a leg on which a cast or brace has been placed. For example, U.S. Pat. No. 4,854,313 to Kloepper discloses a surgical leg stressing device, and more particularly a surgical accessory for imposing a controlled and appropriate stress to a surgical joint during arthroscopic surgery. The leg stressing device comprises a substantially inelastic fabric defining a sling adapted to be positioned about a selected location of the limb displaced from the joint on which surgery is to be conducted. A transverse handle is secured to the sling and enables the sling to be hand-held and manipulated to impose the required stress from the limb location to the joint.

U.S. Pat. No. 5,014,692 to Rhoades discloses a self-manipulatable assembly for moving a patient's leg in a cast, the assembly including an elongated first strap made of a non-elastic flexible material extending from the ankle portion to the thigh portion of the cast and having closed loops on both ends thereof. A second strap made of flexible hook-and-loop self-locking material encircles the ankle portion of the cast and one of the closed loops of the first strap, and a third strap also made of flexible hook-and-loop self-locking material encircles the thigh portion of the cast and passes through the other closed loop of the first strap. The patient grasps the first strap to manipulate the leg cast.

Other devices which are considered to be representative of the prior art in this area are disclosed in U.S. Pat. No. 4,014,327 to Spiro and U.S. Pat. No. 4,019,503 to Smith.

Despite the foregoing prior art devices, there is still a need in the art for a flexible and removable leg cast/brace handle which both effectively and efficiently assists the user in manipulating and moving a leg on which a cast or brace has been placed. For example, the device disclosed in the aforementioned Rhoades patent provides a single elongated strap, extending longitudinally between an ankle strap and a thigh strap, for the person to grasp when movement or manipulation of the leg is desired. In such a situation, a person's tendency is to grip the longitudinal strap at a point nearest to the thigh strap, but this does not provide sufficient leverage, and the result is expenditure of excessive energy by the person in moving or manipulating the leg with its cast or brace. Even if the strap is grasped closer to the ankle strap, the hand naturally tends to slide along the longitudinal strap upwardly toward the thigh strap making it difficult to lift the leg cast/brace as described above. The provision in the Rhoades device of loops on the ends of the single longitudinal strap is undesirable from the standpoint of ease of orientation and positioning of the straps relative to one another. Furthermore, the Rhoades device comprises several individual parts which may become disconnected and misplaced.

Therefore, there is a need in the prior art for the development of a flexible and removable leg cast/brace handle which is efficient from the standpoint of providing maximum leverage for the user, thereby minimizing the strength necessary to manipulate the leg with its cast or brace. Moreover, there is also a need in the prior art for the development of a one-piece flexible and removable leg cast/brace handle which is readily and easily positioned by the user and has sufficient rigidity and strength to withstand prolonged use.

Summary of the Invention

The present invention generally relates to a flexible and removable leg cast/brace handle, and more particularly, to a leg cast/brace handle which provides a substantial amount of leverage to the user when manipulating the leg with its cast or brace, and which also is sufficiently rigid to prevent wearing out or damage to the handle after prolonged use.

In accordance with the present invention, the leg cast/brace handle comprises a first or upper strap for encircling an upper portion of the leg (nearer the torso), a second or lower strap for encircling a lower portion of the leg (nearer the foot), a longitudinal strap extending between and fixedly interconnecting the first strap with the second strap at a predetermined distance, and at least one length of material configured into a loop-like handle and connected to the longitudinal strap. In one embodiment of the invention, a single loop handle is connected to the longitudinal strap adjacent the second or lower strap. In a second embodiment of the invention, a single loop handle is provided between the ends of the longitudinal strap and is connected thereto adjacent the first and second straps. In a third embodiment of the invention, two loop handles are provided, one extending between an intermediate portion of the longitudinal strap and the first strap, and the other extending between the intermediate portion of the longitudinal strap and the second strap. In all embodiments, the loop handles are secured to the longitudinal strap so as to provide the most effective leverage for the user for lifting the leg cast/brace. The length of the longitudinal strap varies not only dependent upon the size of the person, but also whether the first and second straps are to be connected to the thigh and ankle, respectively, or to another portion of the leg and the ankle, respectively. The device of the present invention is constructed of nylon webbing, a hook-and-loop material known as Velwrap™, and D-rings with sewable tabs. As a result of the use of the hook-and-loop material, the first and second straps can be appropriately adjusted in size to fit the thigh, the ankle or any other portion of the leg or of large or small persons with different leg circumferences.

Therefore, it is a principal object of the present invention to provide a flexible and removable leg cast/brace handle 5,779,655

3 that is easy to connect to the leg cast/brace and provides effective leverage for easy lifting of the leg cast/brace. Another object of the invention is to provide a flexible and removable leg cast/brace handle that is made in one integral piece so that the individual components thereof cannot be lost or misplaced.

It is an additional object of the present invention to provide a leg cast/brace having a single loop handle between the ends of the longitudinal strap and connected to the longitudinal strap adjacent the second or lower strap. It is an additional object of the present invention to provide a leg cast/brace having a single loop handle between the ends of the longitudinal strap and connected thereto adjacent the first and second straps.

It is an additional object of the present invention to provide a leg cast/brace having two loop handles, one extending between an intermediate portion of the longitudinal strap and the first strap, and the other extending between the intermediate portion of the longitudinal strap and the second strap. The above and other objects, and the nature of the invention, will be more clearly understood by reference to the following detailed description, the associated drawings, and the appended claims.

DETAILED DESCRIPTION OF THE INVENTION

The invention will now be described in more detail with reference to the various figures of the drawings.

Prior to describing the invention in detail, it should be noted that the flexible and removable leg cast/brace handle is for use by a person who has injured a leg in such a way that necessitates the use of a brace or cast for a period of time while recuperation takes place. The purpose of the device also presupposes that the leg muscles of the person are either too weak to lift the cast or brace because of trauma from injury or because the weight of the cast or brace is too great to lift easily without assistance.

It should be further noted that, normally, a person with a leg in a cast or brace uses either or both hands to pick up the injured leg and lower it from a bed or table, or requires assistance from another person to do so. The device of the present invention permits the person to manipulate or otherwise move or lift the injured leg using only one hand, thereby freeing the other hand so that it can be used to balance the person. This provides the injured person with greater mobility, independence and safety.

Figure 1:
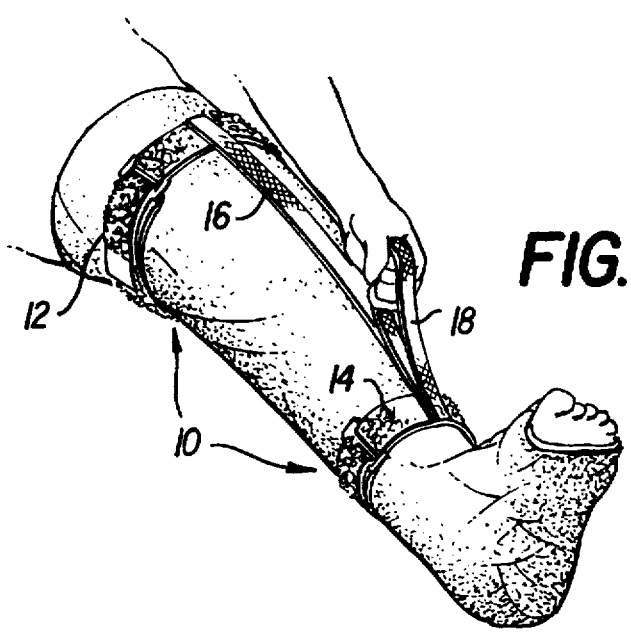
FIG. 1 is a perspective view of one embodiment the device of the present invention shown mounted on the leg of a user.

FIG. 1 is a perspective view of the device of the present invention as mounted on the leg on a user. As seen therein, the device 10 of the present invention comprises a first or upper strap 12, a second or lower strap 14, an interconnecting longitudinal strap 16, and a handle 18. The handle 18 is shown connected to both the lower strap 14 and the longitudinal strap 16, but can be connected to either one of those elements without departing from the scope of the invention. Straps 12, 14 and 16 can be fabricated from any suitable material, but strap 16 is preferably constructed of nylon webbing and upper and lower straps 12, 14 are fabricated from a loop fabric material known as Velwrap™ in the manner described in more detail hereinbelow. Strap 16 is preferably permanently affixed to straps 12, 14 by sewing or other suitable permanent fastening means such as rivets, ultrasonic welding or the like.

Figure 2:
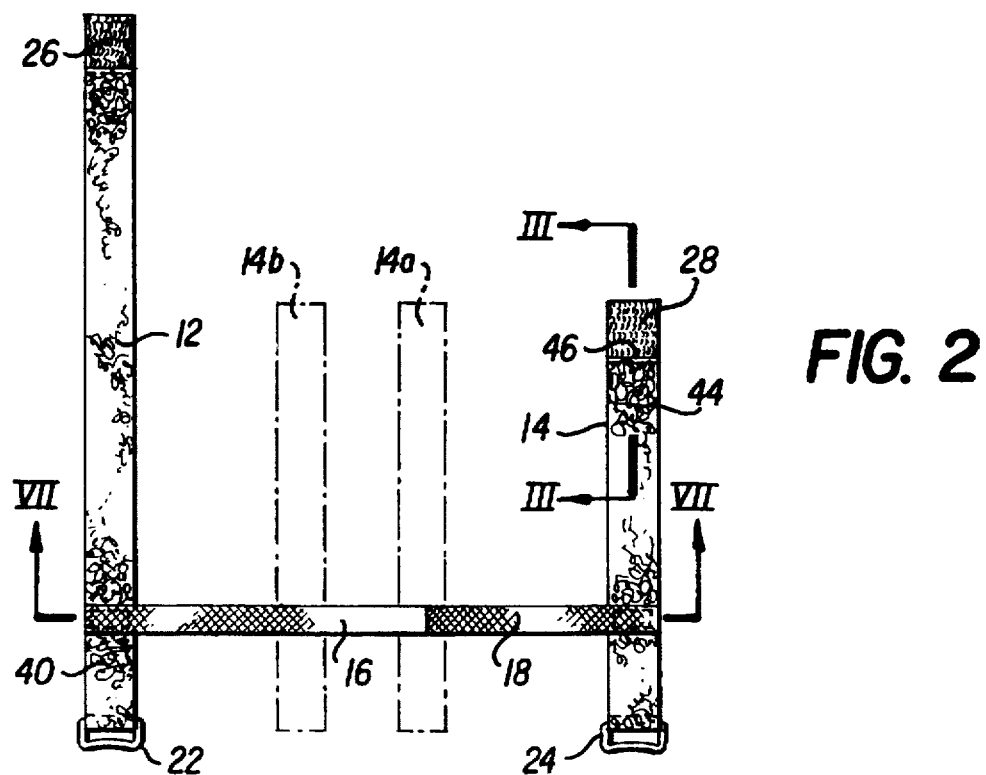
FIG. 2 is a plan view of the webbing strap and hook-and-loop strap portions of the device of the present invention in its assembled condition.

FIG. 2 is a plan view of the various strap portions of the device of the present invention in its assembled state. As seen in FIG. 2, upper strap 12, lower strap 14 and longitudinal strap 16 correspond to identical elements shown in FIG. 1. Thus, upper strap 12 can be employed on the thigh or upper leg of the user, while lower strap 14 can be employed as an ankle strap, and the length of longitudinal strap 16 is fixed accordingly (see FIGS. 7A and 7B discussed below).

However, in accordance with a further embodiment of the present invention, the length of strap 16 is reduced so that lower strap 14 is positioned in the location of lower strap 14a shown in phantom (FIG. 2). In this arrangement, upper strap 12 is positioned at or just above the knee while lower strap 14a serves as an ankle strap (see FIGS. 6A and 6B discussed below). In another embodiment of the invention, longitudinal strap 16 can be further shortened so that strap 14b serves as an ankle strap, while upper strap 12 is positioned below the knee, e.g., at the calf (see FIGS. 5A and 5B discussed below).

As further seen in FIG. 2, the device 10 includes D-rings 22 and 24 connected preferably by sewing to corresponding ends of straps 12 and 14 (or 14a or 14b), while the corresponding other ends of straps 12 and 14 are provided with hook material portions 26 and 28, respectively.

Figure 3:
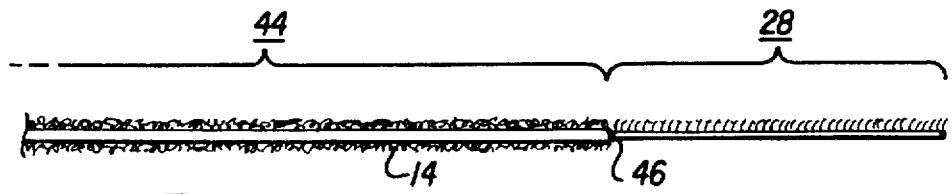
FIG. 3 is a cross-sectional view, taken along section line III—III of FIG. 2, of a portion of the lower or first strap of the device of the present invention.

FIG. 3 is a cross-sectional view, taken along section line III—III of FIG. 2, of a portion of the lower strap 14 of the present invention. As seen therein, strap 14 (and straps 12, 14a and 14b as well) have a hook fabric portion 26 or 28 and a loop fabric material 44, such as Velwrap™ formed on both sides of the straps 12, 14, 14a and 14b. Making the straps 12, 14 of the Velwrap™ material with loops on both sides advantageously provides better gripping of the cast by the straps 12, 14 because of the tendency for the straps to catch on or adhere to rough areas of the cast or brace, thereby helping to prevent slippage during manipulation of the leg cast/brace.

Figure 4:
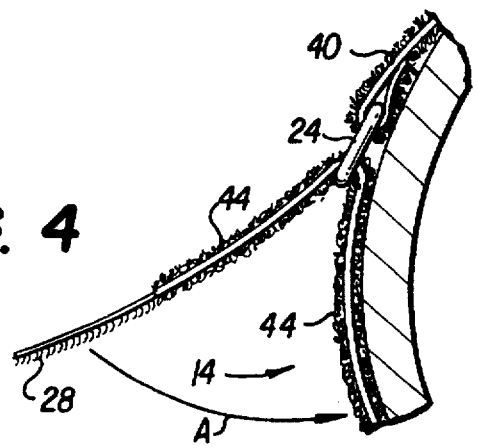
FIG. 4 is a side view of the D-ring assembly employed with each strap of the device of the present invention.

FIG. 4 is a side view of the D-ring assembly employed with each strap of the device of the present invention. As seen therein, D-ring 24 is joined to an end 40 of strap 14 by inserting the end 40 through ring 24, looping it back on itself, and connecting it to itself by stitching. D-rings 24 are preferably provided with sewable tabs (not shown) which are conventional. In mounting the strap 14 (or any of the other straps) on the leg cast or brace of the user, the strap 14 encircles the leg, the hook portion 28 is inserted through D-ring 24, hook 28 is swung in the direction of arrow A (in FIG. 4) into contact with loops 44, thereby achieving a detachable hook-and-loop connection.

Figure 5A:
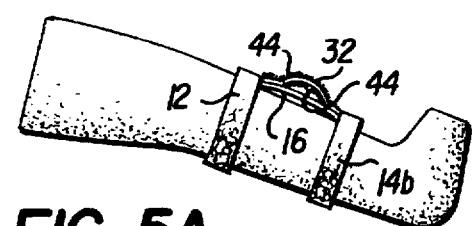
FIGS. 5A and 5B are a side view and a cross-sectional side view taken along section line VII—VII of FIG. 2, respectively, of one embodiment of the invention, as mounted on the leg of a user.
Figure 5B:
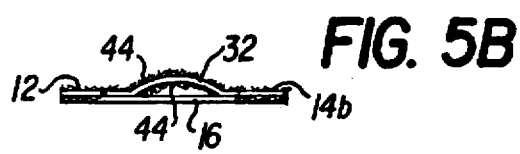

FIGS. 5A and 5B are a side view and a cross-sectional side view, respectively, of one embodiment of the invention, as mounted on the leg of a user. As indicated previously, in this embodiment, strap 12 serves as a lower leg or calf strap, while strap 14b serves as an ankle strap. In accordance with the invention, a loop handle 32 extends from one end of strap 16 (nearest strap 12) to the other end of strap 16 (nearest strap 14b). Handle 32 is fabricated from any suitable material having strength and rigidity, but preferably is fabricated from the same Velwrap™ loop material as the straps 12 and 14, and is stitched to strap 16 at each of its ends. The Velwrap™ material includes loops 44 and is a softer material than the nylon webbing of strap 16, is easier to grasp with the hand and has no sharp edges that might be uncomfortable to the user.

Figure 6A:
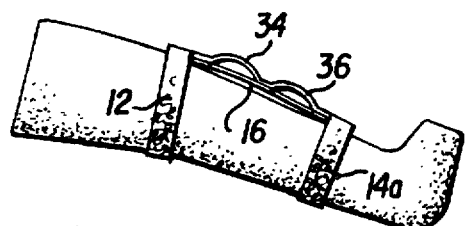
FIGS. 6A and 6B are a side view and a cross-sectional side view taken along section line VII—VII of FIG. 2, respectively, of another embodiment of the invention, as mounted on the leg of a user.
Figure 6B:
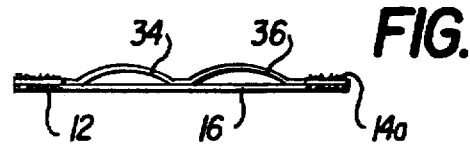

FIGS. 6A and 6B are a side view and a cross-sectional side view, respectively, of another embodiment of the invention, as mounted on the leg of a user. In this embodiment of the invention, strap 12 serves as a knee strap, while strap 14a serves as an ankle strap. In accordance with the invention, two loop handles 34 and 36 are connected to longitudinal strap 16 between straps 12 and 14a. Preferably, the loop handles 34 and 36 are formed by stitching each end of a single length of Velwrap™ material to corresponding ends of strap 16, and then double-stitching the single length of Velwrap™ material and the strap 16 together at their midpoints.

Figure 7A:
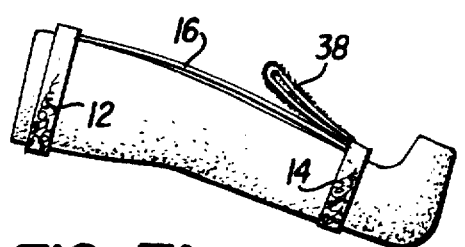
FIGS. 7A and 7B are a side view and a cross-sectional view taken along section line VII—VII of FIG. 2, respectively, of another embodiment of the invention, as mounted on the leg of a user.
Figure 7B:

FIGS. 7A and 7B are a side view and a cross-sectional side view, respectively, of a third embodiment of the invention, as mounted on the leg of a user. In this embodiment of the invention, strap 12 serves as an upper leg or thigh strap, while lower strap 14 serves as an ankle strap. In accordance with the invention, a single loop handle 38 is connected to longitudinal strap 16 nearest strap 14. Preferably, loop handle 38 is formed from a single piece of Velwrap™ material, a lower portion of which is stitched to strap 16. However, as would be evident to those of ordinary skill in the art, handle 38 can be connected to one or both of longitudinal strap 16 and lower strap 14. As mentioned previously, this embodiment is particularly advantageous in that it provides the user with a substantial amount of leverage when raising or lowering the leg with its brace or cast.

It should be noted, as mentioned above, that the device of the present invention is preferably fabricated from nylon webbing, a hook-and-loop fabric material, e.g.,Velwrap™ material, and D-rings with sewable tabs. The loop handle or handles connected to the strap 16 provide the user with a strong and secure means with which to grasp the device. When the user grasps a handle close to the foot or lower leg, an increased amount of leverage is possible.

While preferred forms and arrangements have been shown in illustrating the invention, it is to be understood that various changes and modifications may be made without departing from the spirit and scope of the invention.

I claim:

1. A device for manipulating a leg cast or leg brace of a user, comprising:

a first strap made of a loop fabric material having loops on both sides thereof and located at a first end of the device for encircling a first portion of the cast or brace;

a second strap made of a loop fabric material having loops on both sides thereof and located at a second end of the device for encircling a second portion of the cast or brace;

a third strap extending between and permanently connected to said first strap and said second strap; and a loop handle connected to said third strap and spanning about half a length of said third strap, whereby said user is enabled to grasp the loop handle and manipulate the leg cast or brace.

2. The device of claim 1, wherein said first and second straps each have two ends, a D-ring affixed to one end of each of said first and second straps and a hook fabric portion affixed to the other end of each of said first and second straps.

3. The device of claim 1, wherein said loop handle is formed of a loop fabric material having loops on both sides of said loop handle.

4. The device of claim 3, wherein said third strap is made of nylon webbing.

5. A device for manipulating an immobilized leg of a user, comprising:

first strap means located at a first end of the device for encircling a first portion of the leg;

second strap means located at a second end of the device for encircling a second portion of the leg;

third strap means extending between and joining said first strap means and said second strap means;

a first loop handle having a first end connected to said third strap means and to said second strap means and a second end connected to an intermediate portion of said third strap means; and a second loop handle having one end connected to said intermediate portion of said third strap means and an opposite end connected to said third strap means and said first strap means.

6. The device of claim 5, wherein said first strap means comprises a thigh strap and said second strap means comprises an ankle strap.

7. The device of claim 6, wherein said first loop handle is stitched to the third strap means and the second strap means.

8. The device of claim 5, wherein said first and second strap means are formed of a loop fabric material having loops on both sides of said first and second strap means.

9. The device of claim 8, wherein said first and second strap means each have two ends, a D-ring affixed to one end of each of said first and second strap means and a hook fabric portion affixed to the other end of each of said first and second strap means.

10. The device of claim 5, wherein said first strap means and said second strap means are permanently stitched to said third strap means.

11. The device of claim 5, wherein at least one of said first strap means and said second strap means includes a D-ring for securing said at least one of said first strap means and said second strap means into a closed loop about the leg of the user.

12. The device of claim 11, wherein said D-ring is stitched to said at least one of said first and second strap means.

13. The device of claim 5, wherein a D-ring is stitched to each of said first and second strap means.

14. The device of claim 5, wherein said first and second loop handles are double-stitched to the intermediate portion of said third strap means.

15. The device of claim 5, wherein said loop handles are formed of a loop fabric material having loops on both sides of said loop handles.

16. The device of claim 5, wherein said intermediate portion is at about a halfway point between opposing ends of said third strap means.

17. A device for manipulating a leg cast or leg brace of a user, comprising:

an adjustable first strap located at a first end of the device for encircling a first portion of the cast or brace;

an adjustable second strap located at a second end of the device for encircling a second portion of the cast or brace;

a third strap extending between and permanently connected to said first strap and said second strap, said third strap having a first end connected to said first strap and a second end connected to said second strap; and a dual loop handle connected to said third strap, said handle having one end connected adjacent said first end of said third strap, an opposite end connected adjacent said second end of said third strap, and a middle portion connected to an intermediate portion of said third strap between said first and second ends, wherein said handle spans about an entire length of said third strap.

* * * * *